(12) United States Patent
Gong et al.

(10) Patent No.: US 11,249,061 B2
(45) Date of Patent: Feb. 15, 2022

(54) $NO_X$ SENSOR DIAGNOSTIC SYSTEM AND METHOD

(71) Applicant: Cummins Emission Solutions, Inc., Columbus, IN (US)

(72) Inventors: Jinqian Gong, Columbus, IN (US); Sergio Manuel Hernandez-Gonzalez, Greenwood, IN (US); Ruqiat O. Shifatu-Badru, Columbus, IN (US)

(73) Assignee: Cummins Emission Solutions, Inc., Columbus, IN (US)

( * ) Notice: Subject to any disclaimer, the term of this patent is extended or adjusted under 35 U.S.C. 154(b) by 165 days.

(21) Appl. No.: 16/297,031

(22) Filed: Mar. 8, 2019

(65) Prior Publication Data
US 2019/0204282 A1 Jul. 4, 2019

Related U.S. Application Data

(62) Division of application No. 15/891,944, filed on Feb. 8, 2018, now Pat. No. 10,267,778, which is a division of application No. 14/598,906, filed on Jan. 16, 2015, now Pat. No. 9,927,413.

(51) Int. Cl.
*G01N 33/00* (2006.01)
*F01N 3/20* (2006.01)
*G01N 27/417* (2006.01)

(52) U.S. Cl.
CPC ....... *G01N 33/0037* (2013.01); *F01N 3/2066* (2013.01); *G01N 27/4175* (2013.01); *G01N 33/007* (2013.01); *F01N 2560/026* (2013.01); *Y02A 50/20* (2018.01)

(58) Field of Classification Search
None
See application file for complete search history.

(56) References Cited

U.S. PATENT DOCUMENTS

| 8,327,620 | B2 | 12/2012 | Van Nieuwstadt et al. |
| 8,486,255 | B2 | 7/2013 | Allmendinger |
| 2001/0054282 | A1* | 12/2001 | Lang ............. F02D 41/028 60/277 |
| 2007/0119708 | A1 | 5/2007 | Oya et al. |

(Continued)

FOREIGN PATENT DOCUMENTS

DE  10 2009 046 232 A1  5/2011

OTHER PUBLICATIONS

Office Action issued for German Patent Application No. 102016100403. 0, dated May 11, 2021.

*Primary Examiner* — Blake A Tankersley
(74) *Attorney, Agent, or Firm* — Foley & Lardner LLP

(57) ABSTRACT

A system includes: a $NO_x$ sensor; and a controller configured to: increase an amount of $O_2$ in a chamber of the $NO_x$ sensor; interpret one or more values of a parameter indicative an amount of $O_2$ and/or $NO_x$ measured by the $NO_x$ sensor; determine if the one or more values of the parameter exceed a threshold value; and indicate a failure of the $NO_x$ sensor responsive to the one or more values of the parameter do not exceed the threshold value.

20 Claims, 7 Drawing Sheets

(56) References Cited

U.S. PATENT DOCUMENTS

| | | |
|---|---|---|
| 2008/0011051 A1* | 1/2008 | Lemire ................ G01N 27/419 |
| | | 73/23.31 |
| 2008/0264036 A1 | 10/2008 | Bellovary |
| 2009/0145778 A1 | 6/2009 | Allmendinger |
| 2009/0218220 A1 | 9/2009 | Matter et al. |
| 2010/0083743 A1* | 4/2010 | Wehmeier .......... G01N 27/4175 |
| | | 73/114.72 |
| 2011/0000290 A1 | 1/2011 | Sawada et al. |
| 2011/0016949 A1 | 1/2011 | Sasaki |
| 2011/0023459 A1 | 2/2011 | Nieuwstadt et al. |
| 2011/0252767 A1 | 10/2011 | Lin et al. |
| 2012/0055789 A1 | 3/2012 | Swartz et al. |

\* cited by examiner

$NO_x$ SENSOR DIAGNOSTIC SYSTEM AND METHOD

CROSS-REFERENCE TO RELATED APPLICATIONS

This application is a divisional of U.S. patent application Ser. No. 15/891,944 filed on Feb. 8, 2018, which is a divisional of U.S. patent application Ser. No. 14/598,906 filed Jan. 16, 2015. The contents of both applications are hereby incorporated by reference in their entireties.

TECHNICAL FIELD

The present application relates generally to the field of selective catalytic reduction (SCR) systems for an exhaust aftertreatment system.

BACKGROUND

For internal combustion engines, such as diesel engines, nitrogen oxide ($NO_x$) compounds may be emitted in the exhaust. To reduce $NO_x$ emissions, a SCR process may be implemented to convert the $NO_x$ compounds into more neutral compounds, such as diatomic nitrogen, water, or carbon dioxide, with the aid of a catalyst and a reductant. The catalyst may be included in a catalyst chamber of an exhaust system, such as that of a vehicle or power generation unit. A reductant such as anhydrous ammonia, aqueous ammonia, or urea is typically introduced into the exhaust gas flow prior to the catalyst chamber. To introduce the reductant into the exhaust gas flow for the SCR process, an SCR system may dose or otherwise introduce the reductant through a dosing module that vaporizes or sprays the reductant into an exhaust pipe of the exhaust system up-stream of the catalyst chamber. The SCR system may include one or more sensors to monitor conditions within the exhaust system.

In some instances, $NO_x$ sensors may fail and output values indicative of an amount of $NO_x$ at a low level despite increases in $NO_x$ concentration. In some instances, this may be especially problematic at the exit of an exhaust system when $NO_x$ concentrations are expected to be minimal and have minimal variations.

SUMMARY

Various embodiments relate to a system including a $NO_x$ sensor and a controller. The controller is configured to interpret one or more values of a parameter indicative an amount of $O_2$ and/or $NO_x$ measured by the $NO_x$ sensor responsive to the $NO_x$ sensor reaching an operational temperature and an oxygen pump of the $NO_x$ sensor has not been activated. The controller is further configured to determine if the one or more values of the parameter exceed a threshold value and indicate a failure of the $NO_x$ sensor responsive to the one or more values of the parameter not exceeding the threshold value.

Other embodiments relate to a system including a $NO_x$ sensor and a controller. The controller is configured to increase an amount of $O_2$ in a chamber of the $NO_x$ sensor. The controller is also configured to interpret one or more values of a parameter indicative an amount of $O_2$ and/or $NO_x$ measured by the $NO_x$ sensor. The controller is further configured to determine if the one or more values of the parameter exceed a threshold value and indicate a failure of the $NO_x$ sensor responsive to the one or more values of the parameter not exceeding the threshold value.

Further embodiments relate to a system including a $NO_x$ sensor and a controller. The controller is configured to interpret one or more values of a parameter indicative an amount of $O_2$ and/or $NO_x$ measured by the $NO_x$ sensor responsive to the $NO_x$ sensor reaching an operational temperature and an oxygen pump of the $NO_x$ sensor has not been activated or responsive to increasing an amount of $O_2$ in a chamber of the $NO_x$ sensor. The controller is also configured to calculate a variation of the one or more values of the parameter indicative of the amount of $O_2$ and/or $NO_x$ measured by the $NO_x$ sensor. The controller is configured to determine if the calculated variation exceeds a threshold value and indicate a failure of the $NO_x$ sensor responsive to the calculated variation not exceeding the threshold value.

BRIEF DESCRIPTION OF THE DRAWINGS

The details of one or more implementations are set forth in the accompanying drawings and the description below. Other features, aspects, and advantages of the disclosure will become apparent from the description, the drawings, and the claims, in which:

Figure 1:
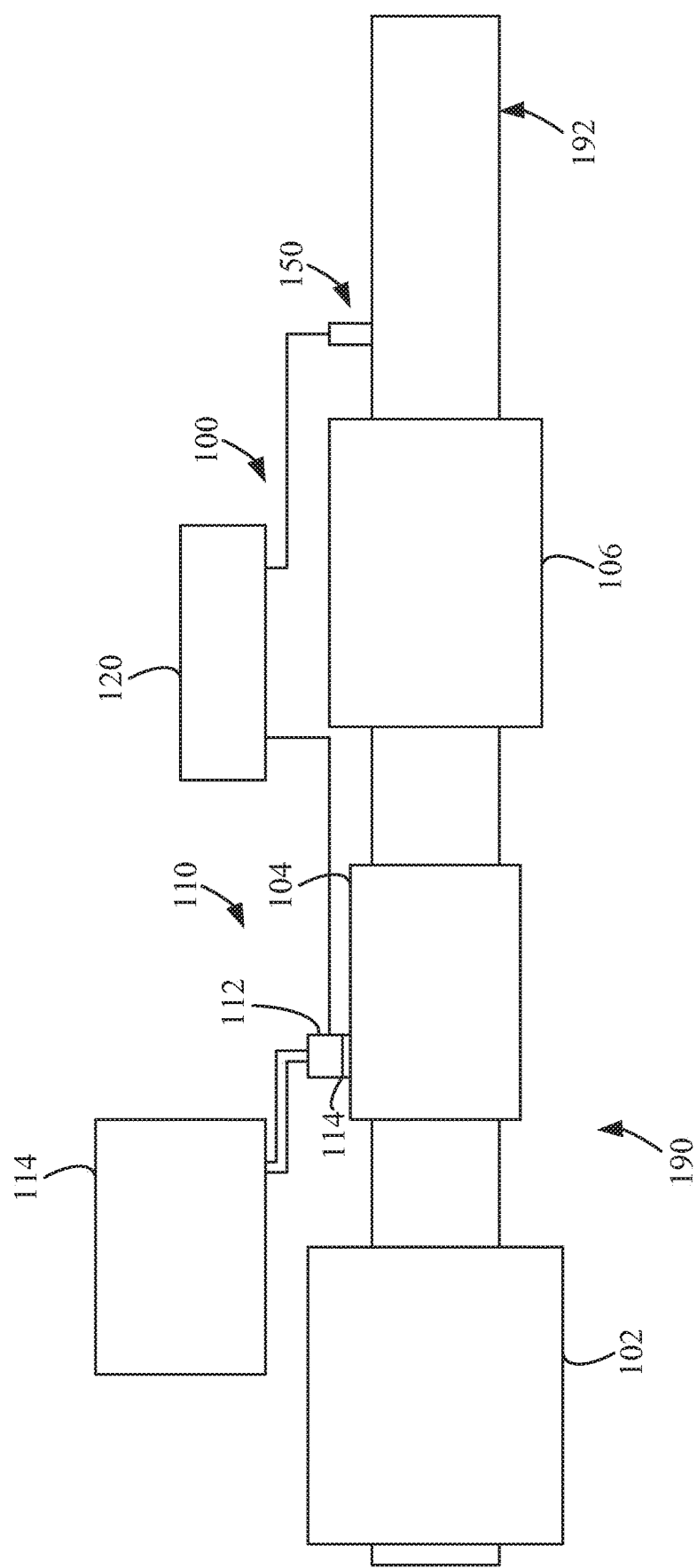
FIG. 1 is a block schematic diagram of an example selective catalytic reduction system having an example reductant delivery system for an exhaust system.

It will be recognized that some or all of the figures are schematic representations for purposes of illustration. The figures are provided for the purpose of illustrating one or more implementations with the explicit understanding that they will not be used to limit the scope or the meaning of the claims.

DETAILED DESCRIPTION

Following below are more detailed descriptions of various concepts related to, and implementations of, methods, apparatuses, and systems for performing a diagnostic check on a $NO_x$ sensor to determine whether the sensor has failed. The various concepts introduced above and discussed in greater detail below may be implemented in any of numerous ways, as the described concepts are not limited to any particular manner of implementation. Examples of specific implementations and applications are provided primarily for illustrative purposes.

I. Overview

In some vehicles, $NO_x$ may be produced with other compounds as a result of combustion, such as for a diesel fuel vehicle, a diesel fuel power generator, etc. In some exhaust systems, a sensor module may be located upstream, downstream, or as part of an SCR catalyst to detect one or more emissions in the exhaust flow after the SCR catalyst. For example, a $NO_x$ sensor may be positioned downstream of the SCR catalyst to detect $NO_x$ within the exhaust gas exiting the exhaust of the vehicle. Such emission sensors may be useful to provide feedback to a controller to modify an operating parameter of the aftertreatment system of the vehicle. For example, a $NO_x$ sensor may be utilized to detect the amount of $NO_x$ exiting the vehicle exhaust system and, if the $NO_x$ detected is too high or too low, the controller may modify an amount of reductant delivered by a dosing module.

A $NO_x$ sensor includes a portion of the $NO_x$ sensor that detects the amount of $NO_x$ present in the exhaust gas sample. The portion of the $NO_x$ sensor that detects the amount of $NO_x$ present in the exhaust gas sample may utilize a $NO_x$ decomposition electrode to decompose $NO_x$ into nitrogen and oxygen ions and utilize a current generated by pumping the oxygen ions through oxygen porous material as representative of the $NO_x$ present in the exhaust gas sample. Because the portion of the $NO_x$ sensor that detects the amount of $NO_x$ present in the exhaust gas sample utilizes oxygen ions as representative of the $NO_x$ present in the exhaust gas sample, the $NO_x$ sensor is cross-sensitive to any oxygen ($O_2$) remaining within the exhaust gas sample. Thus, the $NO_x$ sensor may remove $O_2$ from an exhaust gas sample prior to the portion of the $NO_x$ sensor that detects the amount of $NO_x$ present in the exhaust gas sample. That is, oxygen pumping electrodes present within one or more chambers of the $NO_x$ sensor may be used to extract and pump out $O_2$ present in the exhaust gas sample to reduce the remaining amount of $O_2$ in the exhaust gas sample to a substantially small amount (e.g., 0.001 parts per million (ppm)). Thus, the current generated by pumping oxygen ions through oxygen porous material is substantially representative of the $NO_x$ present in the exhaust gas sample.

In some instances, such as for $NO_x$ sensors at the end of an SCR system or tailpipe out portion of an exhaust system, the amount of $NO_x$ present in the exhaust gas sample may be a very small amount with only minimal variation (e.g., varying by approximately ±5 ppm). Thus, the measurements from the $NO_x$ sensor may be very small and vary in a minimal range during operation. However, in some instances, a $NO_x$ sensor may fail when the portion of the $NO_x$ sensor that detects the amount of $NO_x$ present in the exhaust gas sample registers the same minimal amount of $NO_x$ despite changes to the amount of $NO_x$ present in the exhaust gas sample. For instance, the $NO_x$ decomposition electrode may fail to properly decompose $NO_x$ or other failures with the $NO_x$ sensor may cause the $NO_x$ sensor to be stuck in the minimal range regardless of changes in $NO_x$ concentration. Accordingly, it may be useful to detect when the $NO_x$ sensor is in this stuck-in-range failure mode.

Some $NO_x$ sensor diagnostic implementations utilize high engine-out $NO_x$ spikes to detect changes in measured $NO_x$ by a $NO_x$ sensor to determine whether the $NO_x$ sensor is in a stuck-in-range failure mode. However, with aftertreatment systems that reduce $NO_x$ emissions to very low levels despite these high engine-out $NO_x$ spikes, such spikes may no longer correlate with system outlet $NO_x$ variation, thereby resulting in potentially diagnosing a $NO_x$ sensor as in a stuck-in-range failure mode when the $NO_x$ sensor is actually working properly. Such false-positive failures may result in higher warranty coverage costs, higher replacement part costs, etc.

Moreover, the operation of an engine may be substantially stable, thereby reducing such high engine-out $NO_x$ spikes. As $NO_x$ emissions may be needed or required to be kept at low levels over long periods of time, the lack of high engine-out $NO_x$ spikes may result in a $NO_x$ sensor entering into a stuck-in-range failure mode without being detected for a period of time, thereby potentially releasing unintended $NO_x$ emissions. Thus, it is often desirable to periodically perform a diagnostic check on the $NO_x$ sensor regardless of a high engine-out $NO_x$ spike.

Implementations described herein address methods and systems to detect when the $NO_x$ sensor is in the stuck-in-range failure mode. An engine controller or other diagnostic controller may initiate a diagnostic process when the $NO_x$ sensor initially reaches an operational temperature threshold but prior to reducing the $O_2$ in the exhaust gas sample by using the oxygen pumping electrodes. That is, the diagnostic process may utilize the $O_2$ cross-sensitivity of the portion of the $NO_x$ sensor that detects the amount of $NO_x$ present in the exhaust gas to detect whether the $NO_x$ sensor is in the stuck-in-range failure mode when the $NO_x$ sensor initially reaches its operational temperature. For instance, prior to reducing the $O_2$ in the exhaust gas sample by using the oxygen pumping electrodes, $O_2$ may be present in the second, inner chamber of a $NO_x$ sensor (e.g., approximately 1000 ppm) such that the current generated by pumping the oxygen ions through oxygen porous material should generate a large spike in current when activated based on the presence of the $O_2$ (if 1000 ppm of $O_2$ is present, the current should register a spike corresponding to an approximately 2000 ppm oxygen ion spike based on the 1000 ppm of $O_2$). If such a large spike in current is present, then the $NO_x$ sensor is likely not in the stuck-in-range failure mode. However, if the large spike in current is not present (e.g., the current remains constant or registers minimal changes), then the $NO_x$ sensor may be in the stuck-in-range failure mode. The current may be converted into a numerical value, such as through an A/D converter, to generate a numerical value for a parameter indicative of the $O_2$ and/or $NO_x$ detected by the $NO_x$ sensor.

The engine controller or other diagnostic controller may also initiate a diagnostic process during operation. That is, the diagnostic process may stop or reduce the amount of $O_2$ that is removed from the exhaust gas sample by the oxygen pumping electrodes to increase the amount of $O_2$ present in the second, inner chamber of the $NO_x$ sensor such that the current generated by pumping the oxygen ions through oxygen porous material should generate a large spike in current based on the increased presence of the $O_2$. If such a large spike in current is present, then the $NO_x$ sensor is likely not in the stuck-in-range failure mode. However, if the large spike in current is not present (e.g., the current remains constant or registers minimal changes), then the $NO_x$ sensor may be in the stuck-in-range failure mode.

In some implementations, the change in the parameter indicative of the $O_2$ and/or $NO_x$ detected by the $NO_x$ sensor (e.g., $\Delta DetectedNO_x$) may be stored after each diagnostic process. A counter may be utilized and incremented each time a diagnostic process is run. After a predetermined threshold value for the counter is reached (e.g., 50 times, 100 times, 1000 times, etc.) an average of the changes in the parameters indicative of the $O_2$ and/or $NO_x$ detected by the $NO_x$ sensor during each diagnostic process may be determined and compared to a stored threshold value. If the average change in the parameter indicative of the $O_2$ and/or $NO_x$ detected by the $NO_x$ sensor is below the stored threshold value, a parameter may be set to a value indicating that the $NO_x$ sensor is in the stuck-in-range failure mode, a warning lamp may be lit, such as a malfunction indicator lamp (MIL), and/or other indicators that the $NO_x$ sensor is in the stuck-in-range failure mode may be utilized.

II. Overview of Aftertreatment System

FIG. 1 depicts an aftertreatment system 100 having an example reductant delivery system 110 for an exhaust system 190. The aftertreatment system 100 includes a diesel particulate filter (DPF) 102, the reductant delivery system 110, a decomposition chamber or reactor 104, a SCR catalyst 106, and a sensor probe 150.

The DPF 102 is configured to remove particulate matter, such as soot, from exhaust gas flowing in the exhaust system 190. The DPF 102 includes an inlet, where the exhaust gas is received, and an outlet, where the exhaust gas exits after having particulate matter substantially filtered from the exhaust gas and/or converting the particulate matter into carbon dioxide.

The decomposition chamber 104 is configured to convert a reductant, such as urea, aqueous ammonia, or diesel exhaust fluid (DEF), into ammonia. The decomposition chamber 104 includes a reductant delivery system 110 having a dosing module 112 configured to dose the reductant into the decomposition chamber 104. In some implementations, the urea, aqueous ammonia, DEF is injected upstream of the SCR catalyst 106. The reductant droplets then undergo the processes of evaporation, thermolysis, and hydrolysis to form gaseous ammonia within the exhaust system 190. The decomposition chamber 104 includes an inlet in fluid communication with the DPF 102 to receive the exhaust gas containing $NO_x$ emissions and an outlet for the exhaust gas, $NO_x$ emissions, ammonia, and/or remaining reductant to flow to the SCR catalyst 106.

The decomposition chamber 104 includes the dosing module 112 mounted to the decomposition chamber 104 such that the dosing module 112 may dose a reductant, such as urea, aqueous ammonia, or DEF, into the exhaust gases flowing in the exhaust system 190. The dosing module 112 may include an insulator 114 interposed between a portion of the dosing module 112 and the portion of the decomposition chamber 104 to which the dosing module 112 is mounted. The dosing module 112 is fluidly coupled to one or more reductant sources 116. In some implementations, a pump (not shown) may be used to pressurize the reductant source 116 for delivery to the dosing module 112.

The dosing module 112 is also electrically or communicatively coupled to a controller 120. The controller 120 is configured to control the dosing module 112 to dose reductant into the decomposition chamber 104. The controller 120 may include a microprocessor, an application-specific integrated circuit (ASIC), a field-programmable gate array (FPGA), etc., or combinations thereof. The controller 120 may include memory which may include, but is not limited to, electronic, optical, magnetic, or any other storage or transmission device capable of providing a processor, ASIC, FPGA, etc. with program instructions. The memory may include a memory chip, Electrically Erasable Programmable Read-Only Memory (EEPROM), erasable programmable read only memory (EPROM), flash memory, or any other suitable memory from which the controller 120 can read instructions. The instructions may include code from any suitable programming language.

Figure 3:
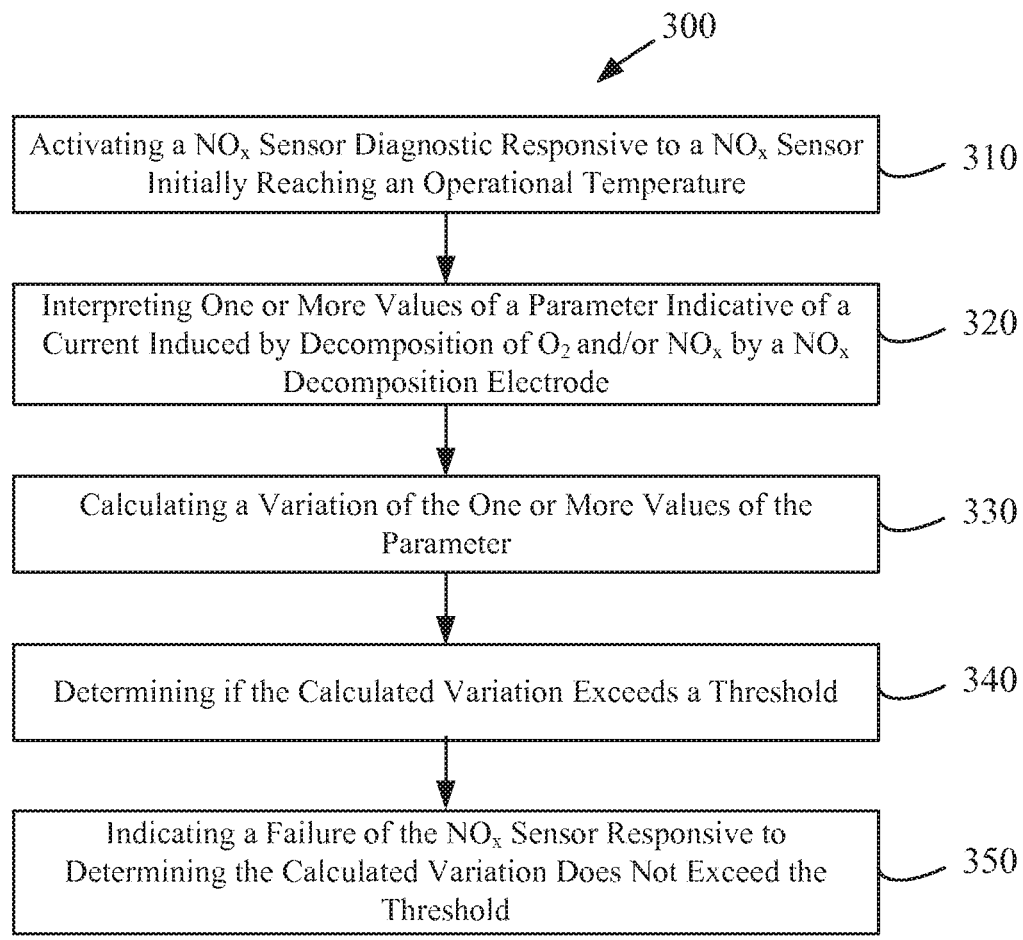
FIG. 3 is a block diagram of an implementation of an exemplary process for detecting a failure of a $NO_x$ sensor when the $NO_x$ sensor reaches an operating temperature.
Figure 4:
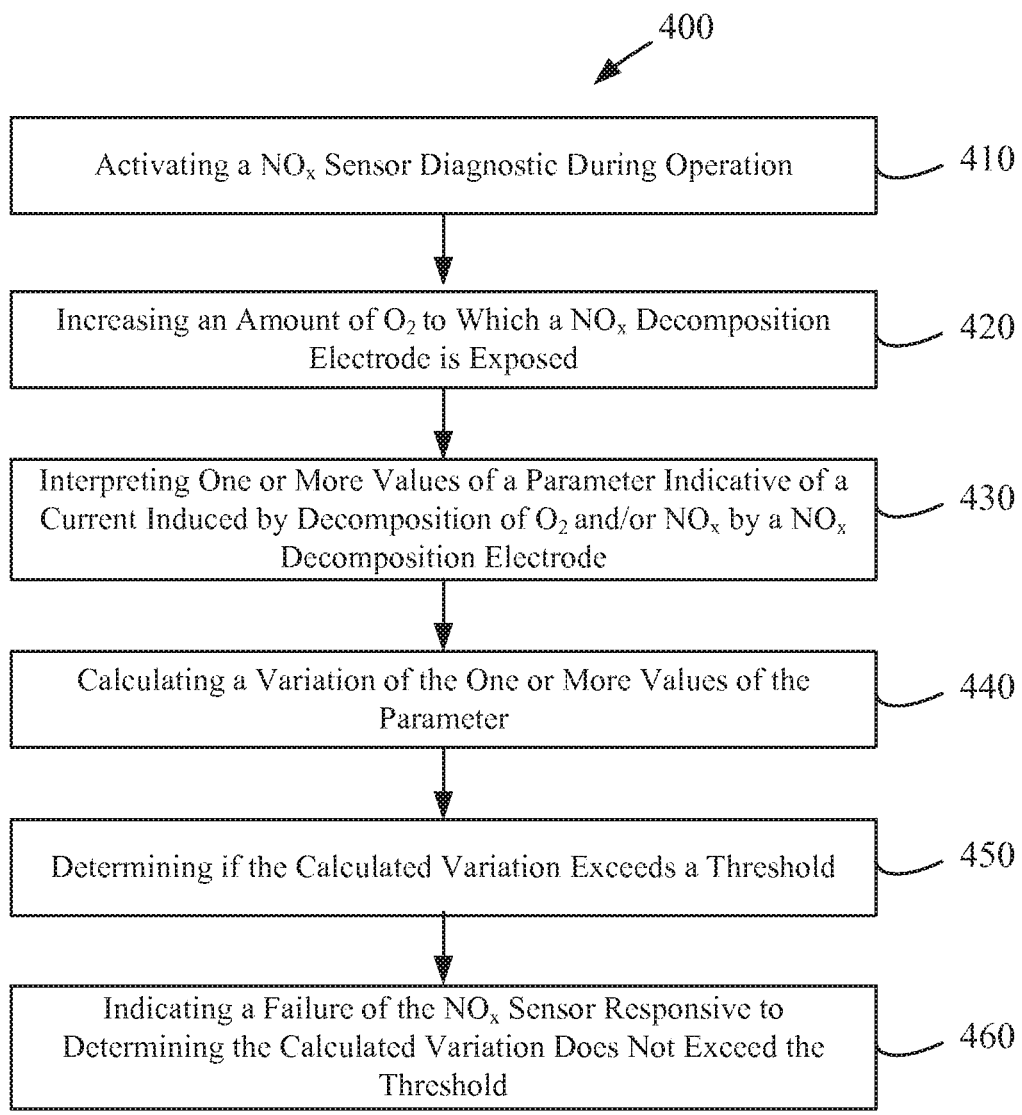
FIG. 4 is a block diagram of an implementation of another exemplary process for detecting a failure of a $NO_x$ sensor during operation.
Figure 5:
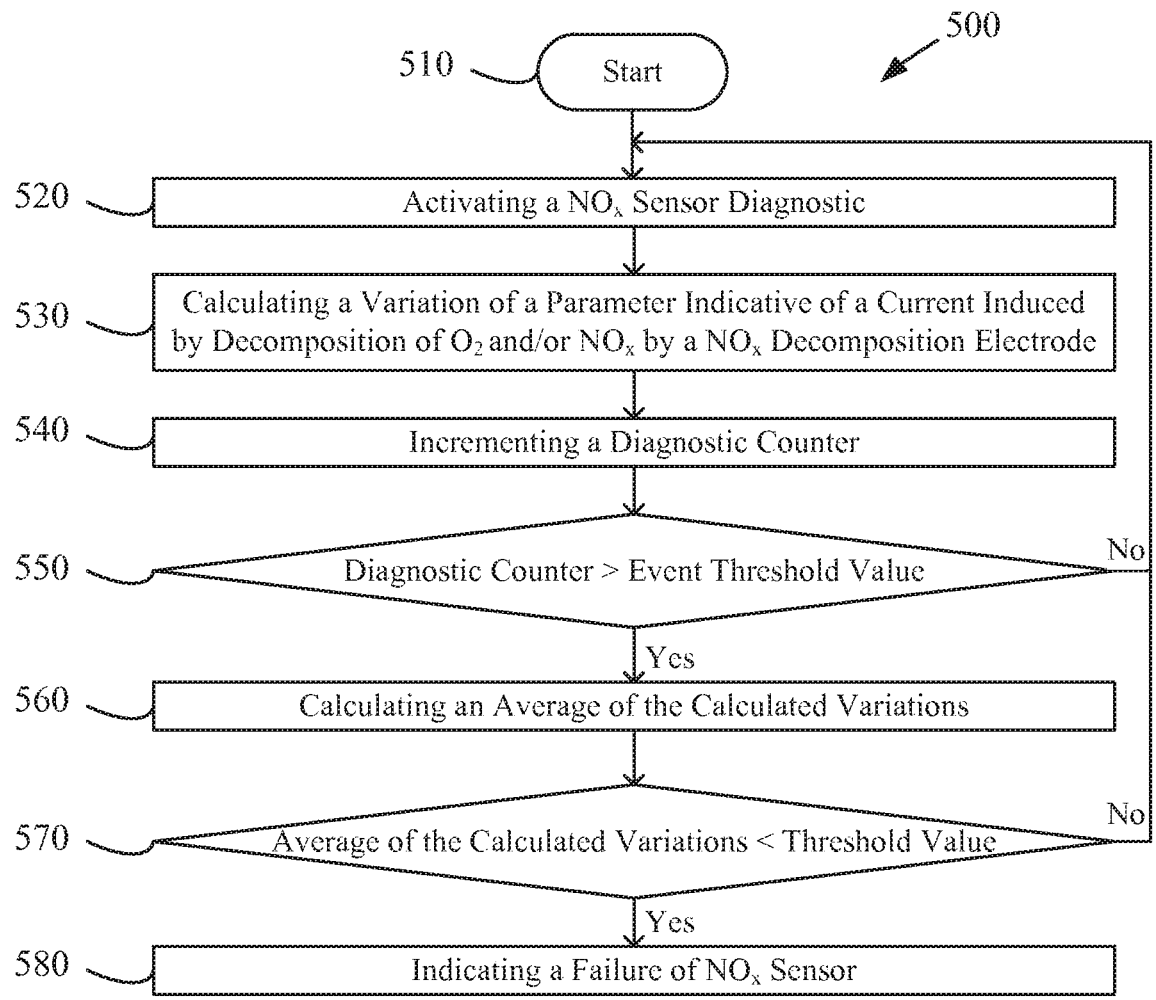
FIG. 5 is a process diagram of an implementation of an exemplary process for detecting a failure of a $NO_x$ sensor when the $NO_x$ sensor reaches an operating temperature or during operation using a counter for determining an average change in a parameter indicative of the $O_2$ and/or $NO_x$ detected by the $NO_x$ sensor over several determined values.

In certain implementations, the controller 120 is structured to perform certain operations, such as those described herein in relation to FIGS. 3-5. In certain implementations, the controller 120 forms a portion of a processing subsystem including one or more computing devices having memory, processing, and communication hardware. The controller 120 may be a single device or a distributed device, and the functions of the controller 120 may be performed by hardware and/or as computer instructions on a non-transient computer readable storage medium.

In certain implementations, the controller 120 includes one or more modules structured to functionally execute the operations of the controller 120. In certain implementations, the controller 120 may include a $NO_x$ sensor diagnostic module for performing the operations described in reference to FIGS. 3-5. The description herein including modules emphasizes the structural independence of the aspects of the controller 120 and illustrates one grouping of operations and responsibilities of the controller 120. Other groupings that execute similar overall operations are understood within the scope of the present application. Modules may be implemented in hardware and/or as computer instructions on a non-transient computer readable storage medium, and modules may be distributed across various hardware or computer based components. More specific descriptions of certain embodiments of controller operations are included in the section referencing FIGS. 3-5.

Example and non-limiting module implementation elements include sensors providing any value determined herein, sensors providing any value that is a precursor to a value determined herein, datalink and/or network hardware including communication chips, oscillating crystals, communication links, cables, twisted pair wiring, coaxial wiring, shielded wiring, transmitters, receivers, and/or transceivers, logic circuits, hard-wired logic circuits, reconfigurable logic circuits in a particular non-transient state configured according to the module specification, any actuator including at least an electrical, hydraulic, or pneumatic actuator, a solenoid, an op-amp, analog control elements (springs, filters, integrators, adders, dividers, gain elements), and/or digital control elements.

The SCR catalyst 106 is configured to assist in the reduction of $NO_x$ emissions by accelerating a $NO_x$ reduction process between the ammonia and the $NO_x$ of the exhaust gas into diatomic nitrogen, water, and/or carbon dioxide. The SCR catalyst 106 includes an inlet in fluid communication with the decomposition chamber 104 from which exhaust gas and reductant is received and an outlet in fluid communication with an end 192 of the exhaust system 190.

The exhaust system 190 may further include a diesel oxidation catalyst (DOC) in fluid communication with the exhaust system 190 (e.g., downstream of the SCR catalyst 106 or upstream of the DPF 102) to oxidize hydrocarbons and carbon monoxide in the exhaust gas.

The sensor probe 150 may be coupled to the exhaust system 190 to detect a condition of the exhaust gas flowing through the exhaust system 190. In some implementations, the sensor probe 150 may have a portion disposed within the exhaust system 190, such as a tip of the sensor probe 150 may extend into a portion of the exhaust system 190. In other implementations, the sensor probe 150 may receive exhaust gas through another conduit, such as a sample pipe extending from the exhaust system 190. While the sensor probe 150 is depicted as positioned downstream of the SCR catalyst 106, it should be understood that the sensor probe 150 may be positioned at any other position of the exhaust system 190, including upstream of the DPF 102, within the DPF 102, between the DPF 102 and the decomposition chamber 104, within the decomposition chamber 104, between the decomposition chamber 104 and the SCR catalyst 106, within the SCR catalyst 106, or downstream of the SCR catalyst 106. In addition, two or more sensor probes 150 may be utilized for detecting a condition of the exhaust gas, such as two, three, four, five, or size sensor probes 150 with each sensor probe 150 located at one of the foregoing positions of the exhaust system 190. In some implementations a first sensor probe 150 may be upstream of the SCR catalyst 106 and a second sensor probe 150 may be downstream of the SCR catalyst 106. In other implementations, the first sensor probe 150 may be upstream of the decomposition chamber 104 and the second sensor probe 150 may be downstream of the SCR catalyst 106. In still other implementations, the first sensor probe 150 may be upstream of the DPF 102, and the sensor probe 150 may be downstream of the SCR catalyst 106. Still further configurations for the sensor probes 150 may be implemented.

III. Implementations of $NO_x$ Sensors

Figure 2:
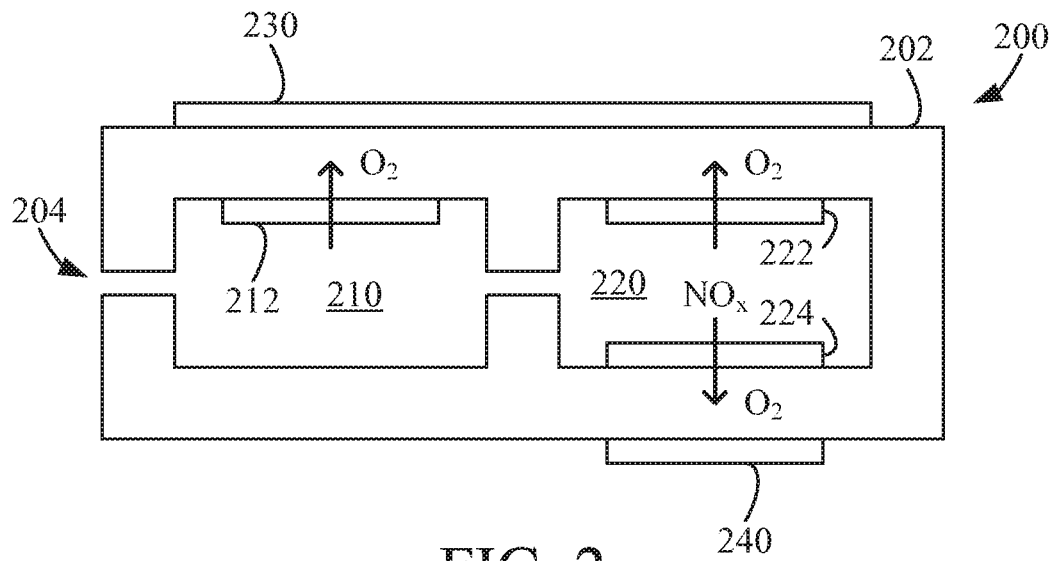
FIG. 2 is a block diagram of an implementation of a $NO_x$ sensor having a first chamber, a second chamber, and a reference chamber.

FIG. 2 depicts a block diagram of an example $NO_x$ sensor 200. The $NO_x$ sensor 200 includes a base 202 that includes an oxygen porous material, such as $ZrO_2$, that permits $O_2$ to be pumped through the material via electrodes on opposing sides of the oxygen porous material of the base 202. An exhaust gas sample from an exhaust system, such as exhaust system 190, is received via an inlet opening 204 in the base 202. In some implementations, the $NO_x$ sensor may have the inlet opening 204 positioned within a portion of the exhaust system and/or an exhaust gas sampling component may direct a portion of the exhaust gas to the inlet opening 204. The base 202 of the $NO_x$ sensor 200 can define a first, outer chamber 210 and a second, inner chamber 220. The first, outer chamber 210 may include an oxygen pumping electrode 212 such that $O_2$ present in an exhaust gas to be sampled by the $NO_x$ sensor 200 may be removed while allowing the $NO_x$ present in the exhaust gas sample to proceed to the second, inner chamber 220. An outer electrode 230 is positioned such that a voltage differential is formed between the oxygen pumping electrode 212 and the outer electrode 230 through the oxygen porous material of the base 202 when a voltage ($V_0$) is applied to the oxygen pumping electrode 212 and the outer electrode 230. The pumping current ($Ip_0$) for the circuit including the oxygen pumping electrode 212 and the outer electrode 230 is proportional to a linear amount of $O_2$ pumped out of the first, outer chamber 210. That is, the amount of $O_2$ pumped out of the first, outer chamber 210 can be regulated based on the voltage ($V_0$) applied to alter the pumping current ($Ip_0$).

$O_2$ is removed via the oxygen pumping electrode 212 because of the cross-sensitivity of a $NO_x$ decomposition electrode 224 of the second, inner chamber 220 to $O_2$. That is, during normal operation, the voltage ($V_0$) can be regulated such that the $O_2$ present in the exhaust gas sample is pumped out when the exhaust gas sample is in the first, outer chamber 210 to reduce the amount of $O_2$ in the exhaust gas sample to a minimal amount, such as approximately 0.001 parts per million (ppm), when the exhaust gas sample enters the second, inner chamber 220 of the $NO_x$ sensor.

In some implementations, the second, inner chamber 220 may also include an oxygen pumping electrode 222 such that additional $O_2$ present in an exhaust gas to be sampled by the $NO_x$ sensor 200 may be removed. The outer electrode 230 and/or a separate outer electrode may be positioned such that a voltage differential is formed between the oxygen pumping electrode 222 and the outer electrode 230 through the oxygen porous material of the base 202 when a voltage ($V_1$) is applied to the oxygen pumping electrode 222 and the outer electrode 230. The pumping current ($Ip_1$) for the circuit including the oxygen pumping electrode 222 and the outer electrode 230 is proportional to a linear amount of $O_2$ pumped out of the second, inner chamber 220. That is, the amount of $O_2$ pumped out of the second, inner chamber 210 can be regulated based on the voltage ($V_1$) applied to alter the pumping current ($Ip_1$). In some implementations, the voltage ($V_1$) can be regulated such that the $O_2$ present in the exhaust gas sample is pumped out to further reduce the amount of $O_2$ in the exhaust gas sample.

The second, inner chamber 220 also includes a $NO_x$ decomposition electrode 224 for the $NO_x$ sensor 200. The $NO_x$ decomposition electrode 224 may be ceramic type metal oxide, such as yttria-stabilized zirconia (YSZ), or any other suitable $NO_x$ decomposition electrode 224. The $NO_x$ decomposition electrode 224 decomposes the $NO_x$ present in the exhaust gas sample into nitrogen and oxygen such that ions can flow through the oxygen porous material of the body 202 to a reference electrode 240 opposite the $NO_x$ decomposition electrode 224 when a voltage ($V_2$) is applied to the $NO_x$ decomposition electrode 224 and the reference electrode 240. The pumping current ($Ip_2$) for the circuit including the $NO_x$ decomposition electrode 224 and the reference electrode 240 is proportional to the oxygen ions pumped out of the second, inner chamber 220 via the $NO_x$ decomposition electrode 224 and the reference electrode 240. Thus, if only minimal amounts of $O_2$ remain in the exhaust gas sample when decomposed by the $NO_x$ decomposition electrode 224, then the resulting pumping current ($Ip_2$) is substantially proportional to the $NO_x$ present in the exhaust gas sample. The pumping current ($Ip_2$) may be measured as representative of the $NO_x$ present in the exhaust gas sample. The measured pumping current ($Ip_2$) may be converted from an analog measured current to a discretized digital value using an A/D converter to generate a numerical value for a parameter indicative of the $NO_x$ present in the exhaust gas sample.

As noted above, the $NO_x$ decomposition electrode 224 is cross-sensitive to $O_2$. Thus, any $O_2$ present in the exhaust gas sample is also decomposed into oxygen ions and will affect the pumping current ($Ip_2$). During operation of the $NO_x$ sensor 200, the oxygen pumping electrodes 212, 222 are used to minimize the amount of $O_2$ present in the exhaust gas sample such that the resulting pumping current ($Ip_2$) is substantially indicative of the $NO_x$ present in the exhaust gas sample. However, such cross-sensitivity of the $NO_x$ decomposition electrode 224 to $O_2$ may be used to determine whether the $NO_x$ sensor 200 is still operating properly or if the $NO_x$ sensor 200 may be in the stuck-in-range failure mode. That is, by using an increased $O_2$ concentration present in the second, inner chamber 220, either when the $NO_x$ sensor 220 first reaches an operating temperature or temporarily during operation, the $NO_x$ sensor 200 may be diagnosed for such a stuck-in-range failure mode.

IV. Implementations of Processes for Detecting Stuck-in-Range Failure of $NO_x$ Sensors FIG. 3 is a block diagram representing an implementation of an exemplary process 300 for detecting a failure of a $NO_x$ sensor, such as $NO_x$ sensor 200 of FIG. 2, when the $NO_x$ sensor reaches an operating temperature. The process 300 may be performed by the controller 120 of FIG. 1, a module of the controller 120 of FIG. 1 (such as a $NO_x$ sensor diagnostic module), or another controller or module.

Before the $NO_x$ sensor warms up to its operating temperature, there is no removal of $O_2$ from the first, outer chamber. Thus, there may be a substantial quantity of $O_2$ present in the second, inner chamber of the $NO_x$ sensor, such as more than 1000 ppm of $O_2$ in the second, inner chamber. When the $NO_x$ sensor reaches its operating temperature, a reading of the $NO_x$ and/or $O_2$ present in the second, inner chamber can be performed (e.g., based on the pumping current ($Ip_2$) that is proportional to the oxygen ions decomposed by $NO_x$ decomposition electrode 224 when a voltage is applied). Because there has been little or no removal of $O_2$ from within the $NO_x$ sensor, the reading of the $NO_x$ and/or $O_2$ present in the second, inner chamber should be high, such as approximately 2000 ppm. If the reading is low, such as under 100 ppm, then this may indicate that the $NO_x$ sensor is in the stuck-in-range failure mode. If the reading is higher than such a low reading, then this may indicate that the $NO_x$ sensor is not in the stuck-in-range failure mode. In some instances, a threshold value indicative of an amount of $O_2$ and/or $NO_x$ of approximately 100 ppm, 500 ppm, 1000 ppm, etc. may be compared to the reading of the $NO_x$ and/or $O_2$ present in the second, inner chamber. Accordingly, implementations of the process 300 for detecting a failure of a $NO_x$ sensor when the $NO_x$ sensor reaches an operating temperature can be used to detect whether the $NO_x$ sensor is in the stuck-in-range failure mode.

The process 300 includes activating a $NO_x$ sensor diagnostic responsive to a $NO_x$ sensor initially reaching an operational temperature (block 310). In some implementations, such as an engine with an aftertreatment system utilizing a system outlet $NO_x$ sensor, when the engine is initially started, the exhaust gas temperature and the $NO_x$ sensor temperature must be raised above one or more temperature thresholds before the $NO_x$ sensor will operate and the aftertreatment system reduces $NO_x$. For instance, after the exhaust system temperature is increased above a dew point, the $NO_x$ sensor may begin to be heated, such as through a heating element of the $NO_x$ sensor and/or a portion of diverted heated exhaust gas. The $NO_x$ sensor may be heated to a predetermined operational temperature before the $NO_x$ sensor is capable of pumping $O_2$ from the first, outer chamber and/or the second, inner chamber to measure NON. Thus, after the $NO_x$ sensor initially reaches an operational temperature, but before $O_2$ pumping begins to reduce the amount of $O_2$ present in the chambers of the $NO_x$ sensor, a $NO_x$ sensor diagnostic may be activated (block 310). As $O_2$ remains in the second, inner chamber of the $NO_x$ sensor, if the $NO_x$ decomposition electrode and reference electrode of the $NO_x$ sensor have a voltage applied, the $NO_x$ decomposition electrode decomposes any $O_2$ and $NO_x$ in the second, inner chamber.

The resulting pumping current ($Ip_2$) can be measured and converted into a discretized numerical value (e.g., via an A/D converter) proportional to the oxygen ions decomposed by the $NO_x$ decomposition electrode. Thus, any $O_2$ present in the exhaust gas sample is also decomposed into oxygen ions and will affect the measured pumping current ($Ip_2$). The discretized numerical value of the measured current ($Ip_2$) can be associated with a parameter, such as a parameter for the sampled oxygen/$NO_x$ (SONOX). In some implementations, the parameter and the associated discretized numerical value for the measured current ($Ip_2$) may be stored in a data storage device, such as a memory. The memory may include a memory chip, Electrically Erasable Programmable Read-Only Memory (EEPROM), erasable programmable read only memory (EPROM), flash memory, or any other suitable memory from which data may be written and read from. In some implementations, the data storage may be part of a controller, such as controller 120 of FIG. 1.

The process 300 includes interpreting one or more values of a parameter indicative of a current induced by decomposition of $O_2$ and/or $NO_x$ by a $NO_x$ decomposition electrode (block 320). As noted above, the $NO_x$ decomposition electrode disassociates any $O_2$ and $NO_x$ in the second, inner chamber, and the resulting pumping current ($Ip_2$) can be measured and converted into a discretized numerical value (e.g., via an A/D converter) proportional to the oxygen ions decomposed by the $NO_x$ decomposition electrode. The discretized numerical value of the measured current ($Ip_2$) can be associated with a parameter, such as a parameter for the sampled oxygen/$NO_x$ (SONOX). In some implementations, the interpretation of the one or more values of the parameter indicative of the current induced by decomposition of $O_2$ and/or $NO_x$ by a $NO_x$ decomposition electrode may be directly interpreted without being stored in a storage device or, in other implementations, the values of the parameter may be retrieved from the storage device to be interpreted. Thus the interpretation of the one or more values of the parameter encompass interpreting a value for the parameter that results from reading a value for the current from the $NO_x$ sensor, either directly or indirectly. In some implementations, several values for the parameter may be interpreted, such as a series of values over a predetermined diagnostic measurement window, such as 1 second, 2 seconds, 3 seconds, 4 seconds, 5 seconds, 10 seconds, etc.

The process 300 also includes calculating a variation of the one or more values of the parameter (block 330). The calculation of the variation may include calculating a difference between a first interpreted value of the parameter and a second interpreted value of the parameter (e.g., a minimum measured value and a maximum measured value during the diagnostic measurement window), between an interpreted value of the parameter and a predetermined value (e.g., a stored diagnostic base value), and/or between an interpreted value of the parameter and a previously interpreted value of the parameter (e.g., from a prior diagnostic test). The calculated variation may be a change in the parameter proportional to the $O_2$ and/or $NO_x$ detected by the $NO_x$ sensor (e.g., $\Delta DetectedNO_x$).

The process 300 further includes determining if the calculated variation exceeds a threshold (block 340). The threshold may be a predetermined value stored in a data storage device, such as a memory, to be accessed when determining if the calculated variation exceeds the threshold. The predetermined value may be an empirically determined value such that, when the calculated variation does not exceed the predetermined value, the $NO_x$ sensor is likely in the stuck-in-range failure mode. The predetermined value may be a value indicative of an amount of $O_2$ and/or $NO_x$ of approximately 100 ppm, 500 ppm, 1000 ppm, etc. In some implementations, the predetermined value may be a value indicative of an amount of $O_2$ and/or $NO_x$ of less than 100 ppm, less than 500 ppm, less than 1000 ppm, etc. The determination of if the calculated variation exceeds the threshold may include subtracting the calculated variation from the threshold and determining whether the resulting value is above, below, or equal to zero.

The process 300 also includes indicating a failure of the $NO_x$ sensor responsive to determining the calculated variation does not exceed the threshold (block 350). In some implementations, indicating a failure of the $NO_x$ sensor may include setting a value for a parameter to a value indicating that the $NO_x$ sensor is in the stuck-in-range failure mode (e.g., setting NOxSensorFail=1 if the $NO_x$ sensor is in the stuck-in-range failure mode), causing a warning lamp to be lit (e.g., a malfunction indicator lamp (MIL)), and/or other setting any other indicators that the $NO_x$ sensor is in the stuck-in-range failure mode. In some implementations, other processes may be triggered and/or stopped responsive to determining the calculated variation does not exceed the threshold and/or the indicated failure of the $NO_x$ sensor. In some implementations, indicating a failure of the $NO_x$ sensor may be responsive to a predetermined number of calculated variations not exceeding the threshold, such as indicating a failure of the $NO_x$ sensor if 10 calculated variations do not exceed the threshold from a sample of 20 calculated variations, thereby reducing the likelihood of a false-positive indication of a failed $NO_x$ sensor.

FIG. 4 depicts a block diagram of an implementation of another exemplary process 400 for detecting a failure of a $NO_x$ sensor, such as $NO_x$ sensor 200 of FIG. 2, during operation. The process 400 may be performed by the controller 120 of FIG. 1, a module of the controller 120 of FIG. 1 (such as a $NO_x$ sensor diagnostic module), or another controller or module.

The process 400 may include activating a $NO_x$ sensor diagnostic during operation (block 410). In some implementations, the activating of the $NO_x$ sensor diagnostic during operation may occur responsive to a timer reaching a threshold, such as activating the $NO_x$ sensor diagnostic at predetermined time intervals. In other implementations, the activating of the $NO_x$ sensor diagnostic may be activated responsive to another event triggering the activation of the $NO_x$ sensor diagnostic.

The process 400 includes increasing an amount of $O_2$ to which a $NO_x$ decomposition electrode is exposed (block 420). The increasing of the amount of $O_2$ may be effected by reducing or stopping the amount of $O_2$ pumped out of the first, outer chamber and/or second, inner chamber of the $NO_x$ sensor. The reduction of the amount of $O_2$ being pumped out may be done via reducing or disconnecting the voltage applied to the corresponding oxygen pumping electrodes, such as oxygen pumping electrode 212 or oxygen pumping electrode 222 of FIG. 2. Thus, the increase in $O_2$ remaining in the second, inner chamber of the $NO_x$ sensor when reducing or stopping the amount of $O_2$ pumped out of via the oxygen pumping electrodes may result in the $NO_x$ decomposition electrode and reference electrode of the $NO_x$ sensor decomposing both the $O_2$ and $NO_x$ in the second, inner chamber. The resulting pumping current ($Ip_2$) can be measured and converted into a discretized numerical value (e.g., via an A/D converter) proportional to the oxygen ions disassociated by the $NO_x$ decomposition electrode. The increased $O_2$ present in the exhaust gas sample is also decomposed into oxygen ions and will affect the measured pumping current ($Ip_2$). The discretized numerical value of the measured current ($Ip_2$) can be associated with a parameter, such as a parameter for the sampled oxygen/$NO_x$ (SONOX). In some implementations, the parameter and the associated discretized numerical value for the measured current ($Ip_2$) may be stored in a data storage device, such as a memory. The memory may include a memory chip, Electrically Erasable Programmable Read-Only Memory (EEPROM), erasable programmable read only memory (EPROM), flash memory, or any other suitable memory from which data may be written and read from. In some implementations, the data storage may be part of a controller, such as controller 120 of FIG. 1.

The process 400 includes interpreting one or more values of a parameter indicative of a current induced by decomposition of $O_2$ and/or $NO_x$ by a $NO_x$ decomposition electrode (block 430). As noted above, the $NO_x$ decomposition electrode decomposes any $O_2$ and $NO_x$ in the second, inner chamber, and the resulting pumping current ($Ip_2$) can be measured and converted into a discretized numerical value (e.g., via an A/D converter) proportional to the oxygen ions decomposed by the $NO_x$ decomposition electrode. The discretized numerical value of the measured current ($Ip_2$) can be associated with a parameter, such as a parameter for the sampled oxygen/$NO_x$ (SONOX). In some implementations, the interpretation of the one or more values of the parameter indicative of the current induced by decomposition of $O_2$ and/or $NO_x$ by a $NO_x$ decomposition electrode may be directly interpreted without being stored in a storage device or, in other implementations, the values of the parameter may be retrieved from the storage device to be interpreted. Thus the interpretation of the one or more values of the parameter encompass interpreting a value for the parameter that results from reading a value for the current from the $NO_x$ sensor, either directly or indirectly. In some implementations, several values for the parameter may be interpreted, such as a series of values over a predetermined diagnostic measurement window, such as 1 second, 2 seconds, 3 seconds, 4 seconds, 5 seconds, 10 seconds, etc.

The process 400 also includes calculating a variation of the one or more values of the parameter (block 440). The calculation of the variation may include calculating a difference between a first interpreted value of the parameter and a second interpreted value of the parameter (e.g., a minimum measured value and a maximum measured value during the diagnostic measurement window), between an interpreted value of the parameter and a predetermined value (e.g., a stored diagnostic base value), and/or between an interpreted value of the parameter and a previously interpreted value of the parameter (e.g., from a prior diagnostic test). The calculated variation may be a change in the parameter proportional to the $O_2$ and/or $NO_x$ detected by the $NO_x$ sensor (e.g., $\Delta DetectedNO_x$).

The process 400 further includes determining if the calculated variation exceeds a threshold (block 450). The threshold may be a predetermined value stored in a data storage device, such as a memory, to be accessed when determining if the calculated variation exceeds the threshold. The predetermined value may be an empirically determined value such that, when the calculated variation does not exceed the predetermined value, the $NO_x$ sensor is likely in the stuck-in-range failure mode. The predetermined value may be a value indicative of an amount of $O_2$ and/or $NO_x$ of approximately 100 ppm, 500 ppm, 1000 ppm, etc. In some implementations, the predetermined value may be a value indicative of an amount of $O_2$ and/or $NO_x$ of less than 100 ppm, less than 500 ppm, less than 1000 ppm, etc. The determination of whether the calculated variation exceeds the threshold may include subtracting the calculated variation from the threshold and determining whether the resulting value is above, below, or equal to zero.

The process 400 also includes indicating a failure of the $NO_x$ sensor responsive to determining the calculated variation does not exceed the threshold (block 460). In some implementations, indicating a failure of the $NO_x$ sensor may include setting a value for a parameter to a value indicating that the $NO_x$ sensor is in the stuck-in-range failure mode (e.g., setting NOxSensorFail=1 if the $NO_x$ sensor is in the stuck-in-range failure mode), causing a warning lamp to be lit (e.g., a malfunction indicator lamp (MIL)), and/or other setting any other indicators that the $NO_x$ sensor is in the stuck-in-range failure mode. In some implementations, other processes may be triggered and/or stopped responsive to determining the calculated variation does not exceed the threshold and/or the indicated failure of the $NO_x$ sensor. In some implementations, indicating a failure of the $NO_x$ sensor may be responsive to a predetermined number of calculated variations not exceeding the threshold, such as indicating a failure of the $NO_x$ sensor if 10 calculated variations do not exceed the threshold from a sample of 20 calculated variations, thereby reducing the likelihood of a false-positive indication of a failed $NO_x$ sensor.

FIG. 5 is a process diagram of an implementation of an exemplary process 500 for detecting a failure of a $NO_x$ sensor, such as $NO_x$ sensor 200 of FIG. 2, using a counter for determining an average change in a parameter indicative of the $O_2$ and/or $NO_x$ detected by the $NO_x$ sensor over several determined values. The process 500 may be performed by the controller 120 of FIG. 1, a module of the controller 120 of FIG. 1 (such as a $NO_x$ sensor diagnostic module), or another controller or module.

The process 500 begins (block 510) and includes activating a $NO_x$ sensor diagnostic (block 520). The activation of the $NO_x$ sensor diagnostic may be responsive to a $NO_x$ sensor initially reaching an operational temperature (e.g., as described in reference to FIG. 3) or during operation (e.g., as described in reference to FIG. 4).

The process 500 includes calculating a variation of a parameter indicative of a current induced by decomposition of $O_2$ and/or $NO_x$ by a $NO_x$ decomposition electrode (block 530). As noted above, the $NO_x$ decomposition electrode decomposes any $O_2$ and $NO_x$ in the second, inner chamber, and the resulting induced pumping current ($Ip_2$) can be measured and converted into a discretized numerical value (e.g., via an A/D converter) proportional to the oxygen ions decomposed by the $NO_x$ decomposition electrode. The discretized numerical value of the measured current ($Ip_2$) can be associated with a parameter, such as a parameter for the sampled oxygen/$NO_x$ (SONOX). In some implementations, several values for the parameter may be utilized, such as a series of values over a predetermined diagnostic measurement window, such as 1 second, 2 seconds, 3 seconds, 4 seconds, 5 seconds, 10 seconds, etc.

The calculation of the variation may include calculating a difference between a first value of the parameter and a second value of the parameter (e.g., a minimum measured value and a maximum measured value during the diagnostic measurement window), between a value of the parameter and a predetermined value (e.g., a stored diagnostic base value), and/or between a value of the parameter and a previous value of the parameter (e.g., from a prior diagnostic test). The calculated variation may be a change in the parameter proportional to the $O_2$ and/or $NO_x$ detected by the $NO_x$ sensor (e.g., $\Delta DetectedNO_x$). The calculated variation of the parameter may be stored in a data structure of a data storage device, such as a memory. The memory may include a memory chip, Electrically Erasable Programmable Read-Only Memory (EEPROM), erasable programmable read only memory (EPROM), flash memory, or any other suitable memory from which data may be written and read from. In some implementations, the data storage may be part of a controller, such as controller 120 of FIG. 1.

The process 500 further includes incrementing a diagnostic counter (block 540) and determining if the diagnostic counter is greater than (or, in some implementations, equal to) an event threshold value (block 550). The event threshold value may be a predetermined or preselected number of samples of calculated variations to be used to determine whether the $NO_x$ sensor has failed. The even threshold value may be selected or determined to reduce the likelihood of false-positives indicating the failure of the $NO_x$ sensor. If the diagnostic counter is not greater than the event threshold value (block 550), then the process 500 returns to activating a $NO_x$ sensor diagnostic (block 520), which may be responsive to a $NO_x$ sensor initially reaching an operational temperature (e.g., as described in reference to FIG. 3) or during operation (e.g., as described in reference to FIG. 4). If the diagnostic counter is greater than the event threshold value (block 550), then the process 500 continues.

The process 500 includes calculating an average of the calculated variations (block 560). The calculation of the average of the calculated variations may include accessing stored calculated variations of the parameter from a storage device and dividing by the number of calculated variations. The process 500 further includes determining if the average of the calculated variations is less than (or, in some implementations, and/or equal to) a threshold value (block 570). The threshold may be a predetermined value stored in a data storage device, such as a memory, to be accessed when determining if the average of the calculated variations is less than (or, in some implementations, and/or equal to) the threshold value. The predetermined value may be an empirically determined value such that, when the calculated variation is less than the predetermined value, the $NO_x$ sensor is likely in the stuck-in-range failure mode. The predetermined value may be a value indicative of an amount of $O_2$ and/or $NO_x$ of approximately 100 ppm, 500 ppm, 1000 ppm, etc. In some implementations, the predetermined value may be a value indicative of an amount of $O_2$ and/or $NO_x$ of less than 100 ppm, less than 500 ppm, less than 1000 ppm, etc. If the average of the calculated variations is not less than (or, in some implementations, and/or equal to) the threshold value (block 570), then the process 500 returns to activating a $NO_x$ sensor diagnostic (block 520), which may be responsive to a $NO_x$ sensor initially reaching an operational temperature (e.g., as described in reference to FIG. 3) or during operation (e.g., as described in reference to FIG. 4). If the average of the calculated variations is less than (or, in some implementations, and/or equal to) the threshold value (block 570), then the process 500 continues.

The process 500 includes indicating a failure of a $NO_x$ sensor (block 580) if the average of the calculated variations is less than (or, in some implementations, and/or equal to) the threshold value (block 570). In some implementations, indicating a failure of the $NO_x$ sensor may include setting a value for a parameter to a value indicating that the $NO_x$ sensor is in the stuck-in-range failure mode (e.g., setting NOxSensorFail=1 if the $NO_x$ sensor is in the stuck-in-range failure mode), causing a warning lamp to be lit (e.g., a malfunction indicator lamp (MIL)), and/or other setting any other indicators that the $NO_x$ sensor is in the stuck-in-range failure mode. In some implementations, other processes may be triggered and/or stopped responsive to determining the calculated variation does not exceed the threshold and/or the indicated failure of the $NO_x$ sensor.

Figure 6:
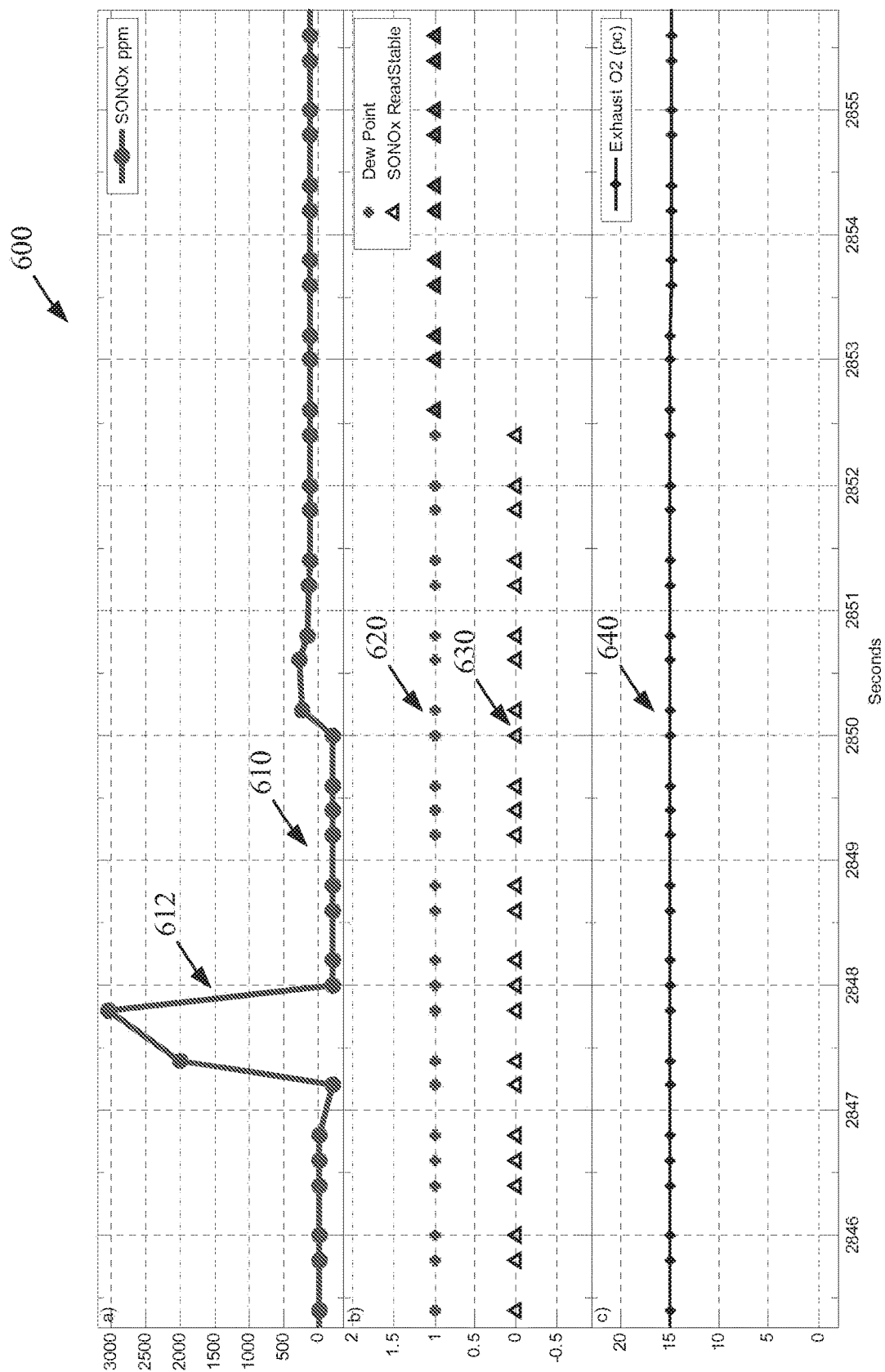
FIG. 6 is a graphical plot of several values for a parameter indicative of a $NO_x$ concentration level from a $NO_x$ sensor, a parameter indicative of whether a dew point has been reached, a parameter indicative of whether a $NO_x$ output value is stable, and a parameter indicative of an $O_2$ concentration level in the exhaust with a spike in the parameter indicative of the $NO_x$ concentration level from the $NO_x$ sensor when the $NO_x$ sensor reaches an operating temperature.

FIG. 6 is a graphical plot 600 of several values over a period of time for a parameter indicative of a $NO_x$ concentration level from a $NO_x$ sensor 610, a parameter indicative of whether a dew point has been reached 620, a parameter indicative of whether a $NO_x$ output value is stable 630, and a parameter indicative of an $O_2$ concentration level in the exhaust 640. The values for the parameter indicative of a $NO_x$ concentration level from a $NO_x$ sensor 610 show a spike 612 when the $NO_x$ sensor reaches an operating temperature and the $O_2$ concentration in the second, inner chamber is measured using the process 300 of FIG. 3. The presence of the spike 612 is indicative of the $NO_x$ sensor not being in a stuck-in-range failure mode as the $NO_x$ sensor measured the large amount of $O_2$ present in the second, inner chamber of the $NO_x$ sensor. If the spike 612 was not present and/or indicated a value or values are below the threshold value, then the $NO_x$ sensor may be indicated as in the stuck-in-range failure mode.

Figure 7:
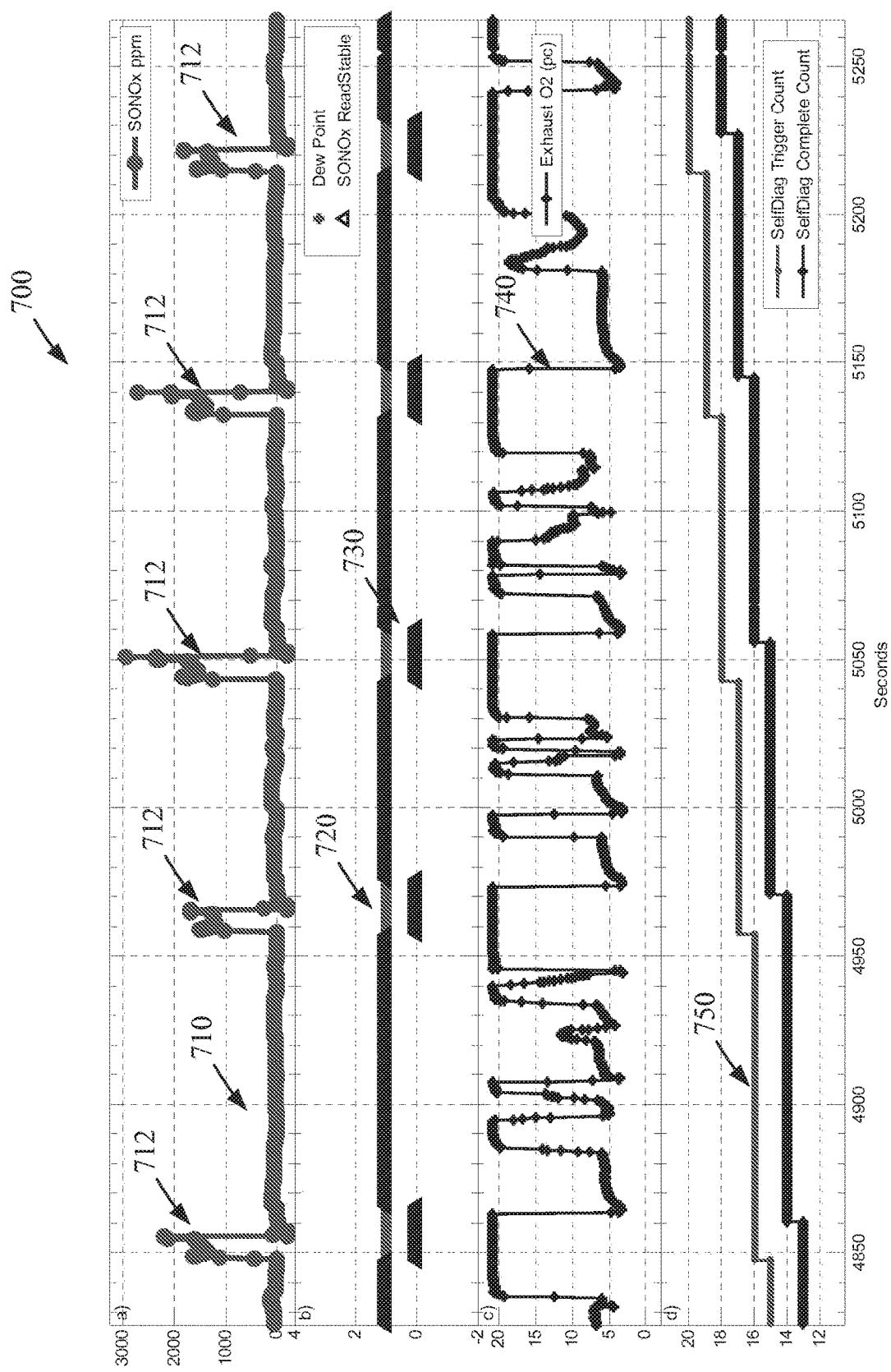
FIG. 7 is a graphical plot of several values for a parameter indicative of a $NO_x$ concentration level from a $NO_x$ sensor, a parameter indicative of whether a dew point has been reached, a parameter indicative of whether a $NO_x$ output value is stable, a parameter indicative of an $O_2$ concentration level in the exhaust, and parameters indicative of a diagnostic trigger count and a diagnostic completion count with several spikes in the parameter indicative of the $NO_x$ concentration level from the $NO_x$ sensor during operation.

FIG. 7 is another graphical plot 700 of several values for a parameter indicative of a $NO_x$ concentration level from a $NO_x$ sensor 710, a parameter indicative of whether a dew point has been reached 720, a parameter indicative of whether a $NO_x$ output value is stable 730, a parameter indicative of an $O_2$ concentration level in the exhaust 740 and parameters indicative of a diagnostic trigger count and a diagnostic completion count 750.

The values for the parameter indicative of a $NO_x$ concentration level from a $NO_x$ sensor 710 showing several spikes 712 during operation, such as might be measured implementing process 400 of FIG. 4. The presence of the spikes 712 is indicative of the $NO_x$ sensor not being in a stuck-in-range failure mode as the $NO_x$ sensor measured the increased amount of $O_2$ present in the second, inner chamber of the $NO_x$ sensor during the diagnostic process. If the spikes 712 were not present and/or indicated a value or values are below the threshold value, then the $NO_x$ sensor may be indicated as in the stuck-in-range failure mode.

Figure 8:
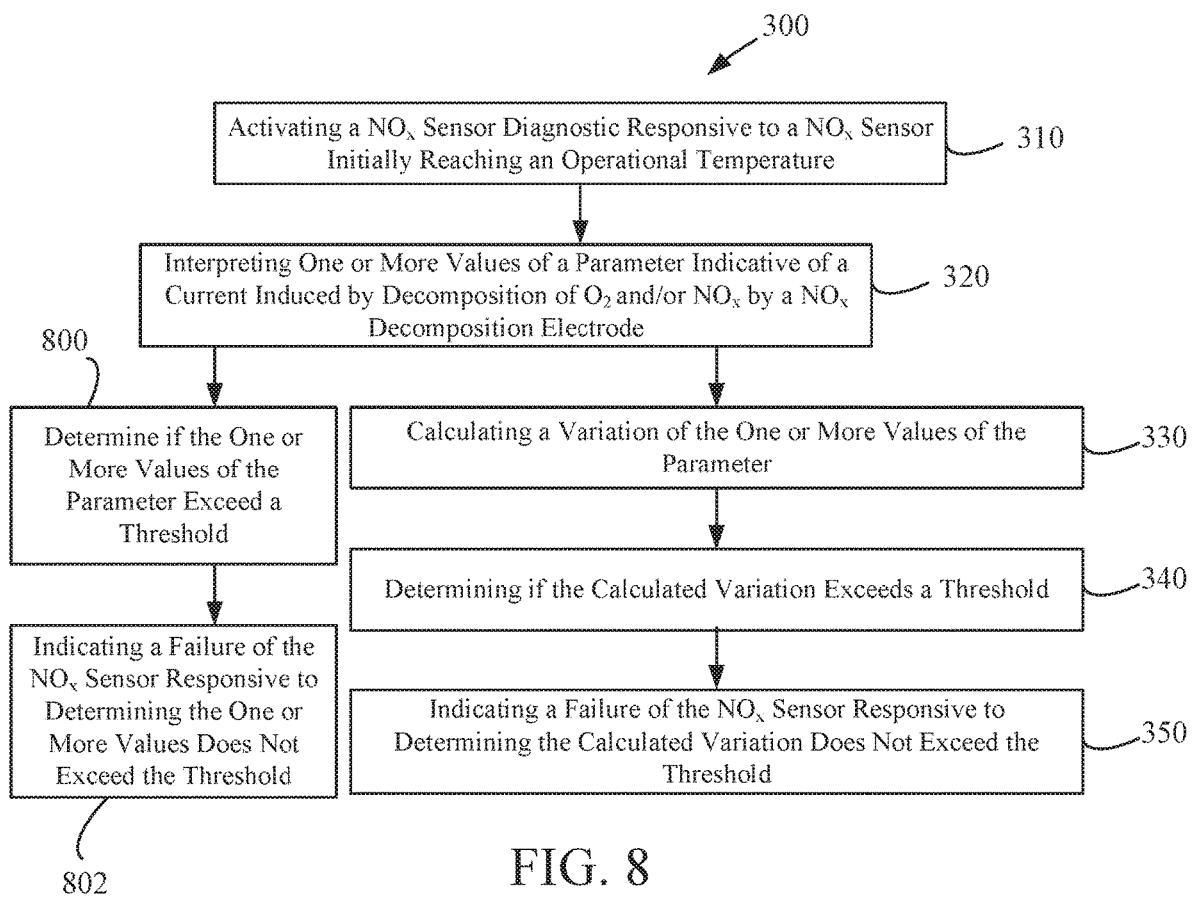
FIG. 8 is a block diagram of an implementation of another exemplary process for detecting a failure of a $NO_x$ sensor when the $NO_x$ sensor reaches an operating temperature.

FIG. 8 is a block diagram representing an implementation of the process 300 for detecting a failure of a $NO_x$ sensor, such as $NO_x$ sensor 200 of FIG. 2, according to one embodiment. The process 300 shown in FIG. 8 may be performed by the controller 120 of FIG. 1, a module of the controller 120 of FIG. 1 (such as a $NO_x$ sensor diagnostic module), or another controller or module. FIG. 8 illustrates that the process 300 is implemented such that the calculation of the variation may be instead replaced by determining if the first interpreted value of the parameter exceeds a threshold value (e.g., the predetermine value, the previously interpreted value of the parameter, etc.) (block 800). FIG. 8 also illustrates that the process 300 is implemented such that indicating a failure of the $NO_x$ sensor responsive to determining the calculated variation does not exceed the threshold may be instead replaced by indicating a failure of the $NO_x$ sensor responsive to determining the one or more values does not exceed the threshold (block 802).

The term "controller" encompasses all kinds of apparatus, devices, and machines for processing data, including by way of example a programmable processor, a computer, a system on a chip, or multiple ones, a portion of a programmed processor, or combinations of the foregoing. The apparatus can include special purpose logic circuitry, e.g., an FPGA or an ASIC. The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as distributed computing and grid computing infrastructures.

A computer program (also known as a program, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code).

While this specification contains many specific implementation details, these should not be construed as limitations on the scope of what may be claimed, but rather as descriptions of features specific to particular implementations. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

As utilized herein, the term "substantially" and any similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided unless otherwise noted. Accordingly, these terms should be interpreted as indicating that insubstantial or inconsequential modifications or alterations of the subject matter described and claimed are considered to be within the scope of the invention as recited in the appended claims. Additionally, it is noted that limitations in the claims should not be interpreted as constituting "means plus function" limitations under the United States patent laws in the event that the term "means" is not used therein.

The terms "coupled," "connected," and the like as used herein mean the joining of two components directly or indirectly to one another. Such joining may be stationary (e.g., permanent) or moveable (e.g., removable or releasable). Such joining may be achieved with the two components or the two components and any additional intermediate components being integrally formed as a single unitary body with one another or with the two components or the two components and any additional intermediate components being attached to one another.

The terms "fluidly coupled," "in fluid communication," and the like as used herein mean the two components or objects have a pathway formed between the two components or objects in which a fluid, such as water, air, gaseous reductant, gaseous ammonia, etc., may flow, either with or without intervening components or objects. Examples of fluid couplings or configurations for enabling fluid communication may include piping, channels, or any other suitable components for enabling the flow of a fluid from one component or object to another.

It is important to note that the construction and arrangement of the system shown in the various exemplary implementations is illustrative only and not restrictive in character. All changes and modifications that come within the spirit and/or scope of the described implementations are desired to be protected. It should be understood that some features may not be necessary and implementations lacking the various features may be contemplated as within the scope of the application, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A system comprising:
   a $NO_x$ sensor comprising:
   a base comprising an inlet opening configured to receive an exhaust gas sample, the base defining:
      a first chamber that is configured to receive the exhaust gas sample from the inlet opening, and
      a second chamber that is configured to communicate with the first chamber and that is separated from the inlet opening by the first chamber;
   a first $O_2$ pumping electrode positioned within the first chamber and operable to pump $O_2$ in the exhaust gas sample out of the first chamber; and
   a $NO_x$ decomposition electrode positioned within the second chamber and operable to decompose $O_2$ and/or $NO_x$ within the second chamber;
   a reference electrode operable with the $NO_x$ decomposition electrode to form a first voltage differential; and
   a controller that is operable to:
      cause the first $O_2$ pumping electrode to pump $O_2$ out of the first chamber;
      cause the $NO_x$ decomposition electrode to decompose $O_2$ and/or $NO_x$ within the second chamber;
      cause the reference electrode and/or the $NO_x$ decomposition electrode to form the first voltage differential;
      determine a parameter indicative of a current associated with the first voltage differential;
      determine a plurality of variations in the parameter over time;
      calculate an average variation based on the variations;
      compare the average variation to a variation threshold; and
      indicate a failure of the $NO_x$ sensor in response to determining that the average variation is less than the variation threshold;
   wherein the variation threshold is indicative of at least one of:
      an amount $O_2$ of between 100 parts per million and 1000 parts per million, inclusive; or
      an amount of $NO_x$ of between 100 parts per million and 1000 parts per million, inclusive.

2. The system of claim 1, further comprising:
   an outer electrode that is positioned outside of the first chamber and the second chamber and opposite of the first $O_2$ pumping electrode, and that is operable with the first $O_2$ pumping electrode to form a second voltage differential through the base;
   wherein the controller is operable to cause the outer electrode and/or the first $O_2$ pumping electrode to form the second voltage differential.

3. The system of claim 2, further comprising a second $O_2$ pumping electrode that is positioned within the second chamber and opposite the outer electrode, and that is operable to pump $O_2$ out of the second chamber.

4. The system of claim 3, wherein:
   the outer electrode is operable with the second $O_2$ pumping electrode to form a third voltage differential through the base;
   the controller is operable to cause the outer electrode and/or the second $O_2$ pumping electrode to form the third voltage differential.

5. The system of claim 4, wherein:
   the reference electrode is positioned outside of the second chamber and opposite the $NO_x$ decomposition electrode; and
   the reference electrode is operable with the $NO_x$ decomposition electrode to form the first voltage differential through the base.

6. The system of claim 5, wherein the base is constructed from an oxygen porous material.

7. The system of claim 5, further comprising:
   an output device operable to display an indication;
   wherein the controller is operable to cause the output device to display the indication in response to detecting a failure of the $NO_x$ sensor.

8. The system of claim 5, wherein the controller is operable to:
   activate a diagnostic associated with the $NO_x$ sensor;
   increment a diagnostic counter after or while determining each of the variations;
   index each of the variations with the diagnostic counter, thereby forming indexed variations;
   compare the diagnostic counter to a counter threshold to determine if the diagnostic counter is greater than the counter threshold; and
   perform the calculation of the average variation in response to determining that the diagnostic counter is greater than the counter threshold, where the variations are the indexed variations.

9. The system of claim 8, wherein:
   the controller is operable to:
      determine a temperature of the $NO_x$ sensor;
      compare the temperature to an operational temperature;
      determine if the temperature is greater than or equal to the operational temperature; and
      activate the diagnostic only in response to determining that the temperature initially becomes greater than or equal to the operational temperature.

10. A system comprising:
    a $NO_x$ sensor comprising:
    a base comprising an inlet opening configured to receive an exhaust gas sample, the base defining:
       a first chamber that is configured to receive the exhaust gas sample from the inlet opening, and
       a second chamber that is configured to communicate with the first chamber and that is separated from the inlet opening by the first chamber;
    a $NO_x$ decomposition electrode positioned within the second chamber and operable to decompose $O_2$ and/or $NO_x$ within the second chamber; and
    a reference electrode operable with the $NO_x$ decomposition electrode to form a voltage differential through the base;
    a controller that is operable to:

cause the $NO_x$ decomposition electrode to decompose $O_2$ and/or $NO_x$ within the second chamber;

cause the reference electrode and/or the $NO_x$ decomposition electrode to form the voltage differential;

determine a parameter indicative of a current associated with the voltage differential;

determine a plurality of variations in the parameter over time;

calculate an average variation based on the variations;

compare the average variation to a variation threshold; and indicate a failure of the $NO_x$ sensor in response to determining that the average variation is less than the variation threshold;

wherein the variation threshold is indicative of at least one of:

an amount $O_2$ of between 100 parts per million and 1000 parts per million, inclusive; or an amount of $NO_x$ of between 100 parts per million and 1000 parts per million, inclusive.

11. The system of claim 10, wherein the controller is operable to:

activate a diagnostic associated with the $NO_x$ sensor;

increment a diagnostic counter after or while determining each of the variations;

index each of the variations with the diagnostic counter, thereby forming indexed variations;

compare the diagnostic counter to a counter threshold to determine if the diagnostic counter is greater than the counter threshold; and perform the calculation of the average variation in response to determining that the diagnostic counter is greater than the counter threshold, where the variations are the indexed variations.

12. The system of claim 11, wherein:

the controller is operable to:

determine a temperature of the $NO_x$ sensor;

compare the temperature to an operational temperature;

determine if the temperature is greater than or equal to the operational temperature; and activate the diagnostic only in response to determining that the temperature initially becomes greater than or equal to the operational temperature.

13. A system comprising:

a $NO_x$ sensor; and a controller that is operable to:

activate a diagnostic associated with the $NO_x$ sensor;

interpret one or more values of a parameter indicative of an amount of $O_2$ and/or $NO_x$ measured by the $NO_x$ sensor;

determine a plurality of variations of the one or more values over time;

calculate an average variation based on the variations;

compare the average variation to a variation threshold; and indicate a failure of the $NO_x$ sensor in response to determining that the average variation is less than the variation threshold;

wherein the variation threshold is indicative of at least one of:

an amount $O_2$ of between 100 parts per million and 1000 parts per million, inclusive; or an amount of $NO_x$ of between 100 parts per million and 1000 parts per million, inclusive.

14. The system of claim 13, wherein:

the controller is further operable to:

determine a temperature of the $NO_x$ sensor;

compare the temperature to an operational temperature;

determine if the temperature is greater than or equal to the operational temperature; and activate the diagnostic only in response to determining that the temperature initially becomes greater than or equal to the operational temperature.

15. The system of claim 13, wherein:

the $NO_x$ sensor comprises a base comprising an inlet opening configured to receive an exhaust gas sample, the base defining:

a first chamber configured to receive the exhaust gas sample from the inlet opening; and a second chamber that is configured to communicate with the first chamber, and that is separated from the inlet opening by the first chamber.

16. The system of claim 15, wherein:

the $NO_x$ sensor further comprises a first $O_2$ pumping electrode that is positioned within the first chamber, and that is configured to be controlled by the controller to pump $O_2$ in the exhaust gas sample out of the first chamber; and the controller is further operable to cause the first $O_2$ pumping electrode to pump the $O_2$ out of the first chamber after interpreting the one or more values.

17. The system of claim 16, wherein:

the $NO_x$ sensor further comprises a $NO_x$ decomposition electrode that is positioned within the second chamber, and that is configured to be controlled by the controller to decompose $O_2$ and/or $NO_x$ within the second chamber by inducing a first amount of current; and the controller is further operable to correlate the first amount of current to the amount of $O_2$.

18. The system of claim 17, wherein:

the $NO_x$ sensor further comprises a second $O_2$ pumping electrode positioned within the second chamber, and that is configured to be controlled by the controller to pump $O_2$ out of the second chamber; and the controller is further operable to cause the second $O_2$ pumping electrode to pump the $O_2$ out of the second chamber after interpreting the one or more values.

19. The system of claim 17, wherein:

the $NO_x$ sensor further comprises a reference electrode outside of the second chamber and opposite the $NO_x$ decomposition electrode, and that is configured to be controlled by the controller to induce a second amount of current; and the controller is further operable to correlate the second amount of current to the amount of $O_2$.

20. The system of claim 13, further comprising:

an output device;

wherein the controller is further operable to indicate the failure of the $NO_x$ sensor by causing the output device to display an indication.

* * * * *